United States Patent
Govari et al.

(10) Patent No.: US 11,903,656 B2
(45) Date of Patent: Feb. 20, 2024

(54) AUTOMATIC CONTROL AND ENHANCEMENT OF 4D ULTRASOUND IMAGES

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 0 days.

(21) Appl. No.: 17/484,696

(22) Filed: Sep. 24, 2021

(65) Prior Publication Data

US 2023/0099952 A1  Mar. 30, 2023

(51) Int. Cl.
*A61B 34/20* (2016.01)
*G06T 7/32* (2017.01)
(Continued)

(52) U.S. Cl.
CPC ............ *A61B 34/20* (2016.02); *A61B 8/0883* (2013.01); *A61B 8/12* (2013.01); *A61B 8/4218* (2013.01); *A61B 8/4254* (2013.01); *A61B 8/4488* (2013.01); *A61B 8/461* (2013.01); *A61B 8/483* (2013.01); *A61B 8/5246* (2013.01); *A61B 8/5269* (2013.01); *A61B 8/54* (2013.01); *G06T 5/20* (2013.01); *G06T 7/32* (2017.01); *A61B 2034/2051* (2016.02); *G06T 2207/10136* (2013.01); *G06T 2207/20048* (2013.01); *G06T 2207/30048* (2013.01)

(58) Field of Classification Search
CPC ...... A61B 8/4218; A61B 34/20; A61B 8/4254; A61B 2034/2051; A61B 8/12; A61B 8/4488
See application file for complete search history.

(56) References Cited

U.S. PATENT DOCUMENTS 6,332,089 B1  12/2001 Acker et al.
6,618,612 B1  9/2003 Acker et al.
(Continued)

FOREIGN PATENT DOCUMENTS

| WO | WO9605768 | 2/1996 |
| WO | WO2020/030665 | 2/2020 |
| WO | WO2020/004117 | 3/2020 |

OTHER PUBLICATIONS

Koolwal, Aditya B. et al, "A Fast Slam Approach to Freehand 3-D Ultrasound Reconstruction for Catheter Ablation Guidance in the Left Atrium," Ultrasound in Medicine and Biology, New York, NY, US, vol. 37, No. 12, Aug. 9, 2011, pp. 2037-2054.

(Continued)

Primary Examiner — Joel Lamprecht
Assistant Examiner — Nyrobi Celestine
(74) Attorney, Agent, or Firm — Gabriel K. Azar

(57) ABSTRACT

A method includes emitting an ultrasound beam, having a predefined field of view (FOV), from an array of ultrasound transducers in a catheter in an organ of a patient. Echo signals are received in the array, in response to the ultrasound beam. A position of a target object is estimated within the FOV. When the estimated position of the target object violates a centering condition, the FOV of the ultrasound beam is automatically modified to re-meet the centering condition.

8 Claims, 4 Drawing Sheets

(51) Int. Cl.
*A61B 8/08* (2006.01)
*A61B 8/12* (2006.01)
*A61B 8/00* (2006.01)
*G06T 5/20* (2006.01)

(56) References Cited

U.S. PATENT DOCUMENTS

| | | |
|---|---|---|
| 11,039,883 B1 | 6/2021 | Boveja et al. |
| 2002/0065455 A1 | 5/2002 | Ben-Haim et al. |
| 2003/0120150 A1 | 6/2003 | Govari |
| 2004/0068178 A1 | 10/2004 | Chang et al. |
| 2004/0254458 A1* | 12/2004 | Govari ............... A61B 5/062 600/437 |
| 2007/0106147 A1* | 5/2007 | Altmann ............... A61B 8/12 600/407 |
| 2007/0225553 A1* | 9/2007 | Shahidi ............... A61B 90/36 600/103 |
| 2008/0287778 A1 | 11/2008 | Li et al. |
| 2013/0231557 A1* | 9/2013 | Li ....................... A61B 8/483 600/424 |
| 2015/0272549 A1 | 10/2015 | Samset et al. |
| 2016/0120499 A1 | 5/2016 | Vignon et al. |
| 2018/0168682 A1* | 6/2018 | Hazard, III ........... A61B 34/20 |
| 2019/0167233 A1 | 6/2019 | Konofagou et al. |
| 2019/0254649 A1* | 8/2019 | Walters ............... A61B 1/05 |
| 2019/0350660 A1* | 11/2019 | Moll ................... A61B 1/273 |
| 2020/0214662 A1 | 7/2020 | Konofagou et al. |
| 2021/0378627 A1* | 12/2021 | Yarmush ............... A61B 8/12 |

OTHER PUBLICATIONS

Extended European Search Report dated Feb. 10, 2023 from corresponding EP application 22197417.3-1126.

* cited by examiner

AUTOMATIC CONTROL AND ENHANCEMENT OF 4D ULTRASOUND IMAGES

FIELD OF THE INVENTION

The present invention relates generally to medical visualization methods, and particularly to visualizing ultrasound data acquired using an intra-body medical ultrasound probe.

BACKGROUND OF THE INVENTION

Ultrasound visualization techniques using data acquired by an ultrasound catheter have been previously proposed in the patent literature. For example, PCT International Patent Publication WO 2020/030665 describes a system for determining a position of an interventional device respective an image plane defined by an ultrasound imaging probe. The position is determined based on ultrasound signals transmitted between the ultrasound imaging probe and an ultrasound transducer attached to the interventional device. An image reconstruction unit provides a reconstructed ultrasound image. A position determination unit computes a position of the ultrasound transducer respective the image plane, and indicates the computed position in the reconstructed ultrasound image. The position determination unit suppresses the indication of the computed position under specified conditions relating to the computed position and the ultrasound signals.

As another example, U.S. Patent Application Publication 2015/0272549 describes an ultrasound imaging system and method for identifying, with a processor, a subset of the ultrasound channel data with a specular reflector signature. The system implements, with the processor, a specular reflector processing technique on the subset of the ultrasound channel data to calculate at least one of a position and an orientation of a specular reflector. The system and method include performing an action based on at least one of a position and orientation of the specular reflector.

U.S. Patent Application Publication 2020/0214662 describes systems and methods for generating an electromechanical map. The methods include obtaining ultrasound data comprising a series of consecutive image frames and radio frequency (RF) signals corresponding to the location in the heart, measuring displacements and strains based on the ultrasound data to determine an electromechanical activation in the location, converting the ultrasound data into a series of isochrone maps, and combining the series of isochrone maps to generate the electromechanical map.

PCT International Publication WO 2020/044117 describes a catheter-based ultrasound imaging system configured to provide a full circumferential 360-degree view around an intra-vascular/intra-cardiac imaging-catheter-head by generating a 3D view of the tissue surrounding the imaging-head over time. The ultrasound imaging system can also provide tissue-state mapping capability. The evaluation of the vasculature and tissue characteristics include path and depth of lesions during cardiac-interventions such as ablation. The ultrasound imaging system comprises a catheter with a static or rotating sensor array tip supporting continuous circumferential rotation around its axis, connected to an ultrasound module and respective processing machinery allowing ultrafast imaging and a rotary motor that translates radial movements around a longitudinal catheter axis through a rotary torque transmitting part to rotate the sensor array-tip. This allows the capture and reconstruction of information of the vasculature including tissue structure around the catheter tip for generation of the three-dimensional view over time.

SUMMARY OF THE INVENTION

An embodiment of the present invention that is described hereinafter provides a method including emitting an ultrasound beam, having a predefined field of view (FOV), from an array of ultrasound transducers in a catheter in an organ of a patient. Echo signals are received in the array, in response to the ultrasound beam. A position of a target object is estimated within the FOV. When the estimated position of the target object violates a centering condition, the FOV of the ultrasound beam is automatically modified to re-meet the centering condition.

In some embodiments, emitting the ultrasound beam includes driving the ultrasound transducers with respective driving signals, and wherein modifying the FOV includes adjusting phases of one or more of the driving signals.

In some embodiments, modifying the FOV includes automatically re-positioning the array relative to the organ.

In an embodiment, re-positioning the array includes estimating a location of a distal end of the catheter using location signals from a location sensor integrated in the distal end, and moving the distal end based on the estimated location. In another embodiment, re-positioning the array relative to the organ includes controlling a handle of the catheter using a robotic arm.

In some embodiments, estimating the position of the target object includes identifying the target object in an ultrasound image using image processing.

There is additionally provided, in accordance with another embodiment of the present invention, a method including acquiring ultrasound images using a catheter, and acquiring corresponding location signals from a location sensor in the catheter. Based on the location signals, a group of the ultrasound images is identified, the images having a matching Field Of View (FOV). The ultrasound images in the group are averaged to produce an enhanced image. The enhanced image is displayed to a user.

In some embodiments, identifying the group includes including in the group ultrasound images that match both in the FOV and in a level of motion of the catheter during acquisition.

In some embodiments, the ultrasound images image at least a portion of a heart, and identifying the group includes including in the group ultrasound images that match both in the FOV and in a cardiac phase of the heart during acquisition.

There is further provided, in accordance with another embodiment of the present invention, a method including acquiring multiple two-dimensional (2D) ultrasound slices using an ultrasound catheter. A Laplace transform is applied to each of the multiple 2D ultrasound slices, to produce respective 2D Laplace-transformed slices. Noise is suppressed in the 2D Laplace-transformed slices. The noise-suppressed Laplace-transformed slices are combined into an inverse three-dimensional (3D) image.

An inverse Laplace transform is applied to the inverse 3D image, to produce a 3D noise-suppressed ultrasound image. The 3D noise-suppressed ultrasound image is displayed to a user.

In some embodiments, suppressing the noise in the 2D Laplace-transformed slices includes applying low-pass filtering to the 2D Laplace-transformed slices.

In some embodiments, combining the noise-suppressed Laplace-transformed slices into the inverse 3D image includes performing registration among the multiple acquired ultrasound slices using signals from a location sensor of the catheter. The noise-suppressed Laplace-transformed slices are combined based on the registration.

There is further provided, in accordance with another embodiment of the present invention, a medical imaging method including inserting an ultrasound probe into an organ of a body, the ultrasound probe including (i) a two-dimensional (2D) ultrasound transducer array, and (ii) a sensor configured to output signals indicative of a position and orientation of the 2D ultrasound transducer array inside the organ. Using the signals output by the sensor, voxel locations are determined in each three-dimensional (3D) image acquired by the 2D ultrasound transducer. Using the determined voxel locations in each 3D image, probe movement is compensated for while averaging the 3D images. Using the averaged 3D images, a voxel-location-compensated rendering is formed, of at least a portion of the organ. The compensated rendering is presented to a user.

There is furthermore provided, in accordance with another embodiment of the present invention, a system, including an array of ultrasound transducers and a processor. The array of ultrasound transducers is in a catheter in an organ of a patient, and the array configured to emit an ultrasound beam, having a predefined field of view (FOV), with the array is further configured to receive echo signals in response to the ultrasound beam. The processor is configured to estimate a position of a target object within the FOV, and, when the estimated position of the target object violates a centering condition, automatically modify the FOV of the ultrasound beam to re-meet the centering condition.

There is additionally provided, in accordance with another embodiment of the present invention, a system including a catheter and a processor. The catheter is configured for acquiring ultrasound images and acquiring corresponding location signals from a location sensor in the catheter. The processor is configured to (i) identify, based on the location signals, a group of the ultrasound images having a matching Field Of View (FOV), (ii) average the ultrasound images in the group, to produce an enhanced image, and (iii) display the enhanced image to a user.

There is additionally more provided, in accordance with another embodiment of the present invention, a system including an ultrasound catheter and a processor. The ultrasound catheter is configured for acquiring multiple two-dimensional (2D) ultrasound slices. The processor is configured to (a) apply a Laplace transform to each of the multiple 2D ultrasound slices, to produce respective 2D Laplace-transformed slices, (b) suppress noise in the 2D Laplace-transformed slices, (c) combine the noise-suppressed Laplace-transformed slices into an inverse three-dimensional (3D) image, (d) apply an inverse Laplace transform to the inverse 3D image, to produce a 3D noise-suppressed ultrasound image, and (e) display the 3D noise-suppressed ultrasound image to a user.

There is further provided, in accordance with another embodiment of the present invention, medical imaging system, including an ultrasound probe and a processor. The ultrasound probe is configured for insertion into an organ of a body, the ultrasound probe including a two-dimensional (2D) ultrasound transducer array, and a sensor configured to output signals indicative of a position and orientation of the 2D ultrasound transducer array inside the organ. The processor is configured to (i) using the signals output by the sensor, determine voxel locations in each three-dimensional (3D) image acquired by the 2D ultrasound transducer, (ii) using the determined voxel locations in each 3D image, compensate for probe movement while averaging the 3D images, (iii) using the averaged 3D images, form a voxel-location-compensated rendering of at least a portion of the organ, and (iv) present the compensated rendering to a user.

The present invention will be more fully understood from the following detailed description of the embodiments thereof, taken together with the drawings in which:

DETAILED DESCRIPTION OF EMBODIMENTS

Overview

Figure 1:
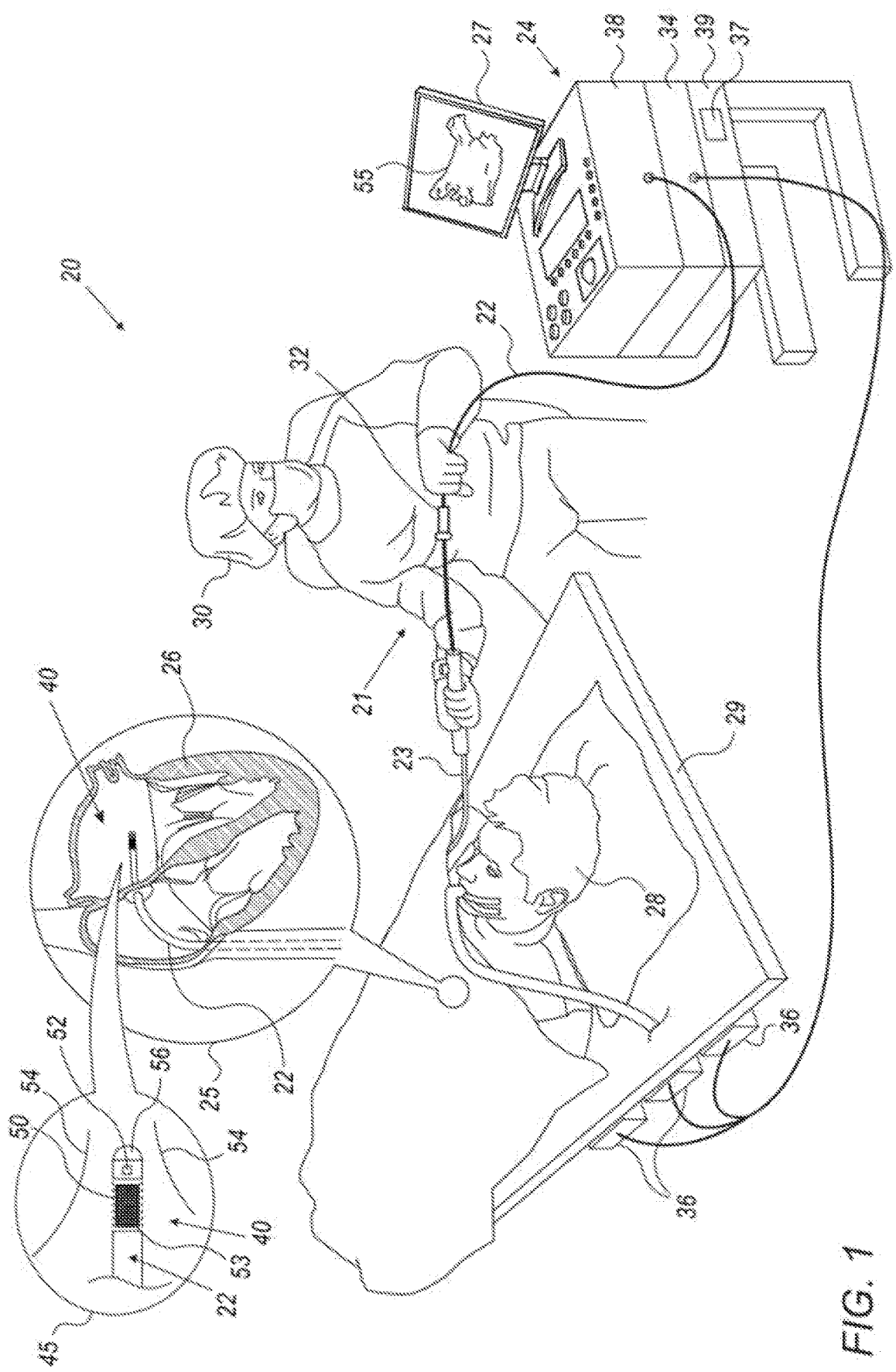
FIG. 1 is a schematic, pictorial illustration of a catheter-based ultrasound imaging system using a catheter with a distal end assembly comprising a 2D ultrasound array and a location sensor, in accordance with an embodiment of the present invention.

Some embodiments of the present invention that are described herein provide methods and systems that use a probe, such as a catheter, having a two-dimensional (2D) array of ultrasound transducers, for producing three-dimensional (3D) or four-dimensional (4D) ultrasound images. In the present context, the term "3D ultrasound image" refers to an ultrasound image that represents a certain volume in three dimensions. The term "4D ultrasound image" refers to a time series of 3D ultrasound images of a certain volume. A 4D image can be regarded as a 3D movie, the fourth dimension being time. Another way of describing a 4D image (or rendering) is as a time dependent 3D image (or rendering).

In some embodiments, the catheter also comprises an integral location sensor, such as a magnetic position sensor, that is pre-registered with the 2D array. The 2D array produces a 3D sector-shaped ultrasound beam occupying a defined solid angle; (such a beam is referred to herein as a "wedge," as opposed to a 1D array "fan"). The 2D array is thus able to image a 2D section of an inner wall of an organ, such as of a cardiac chamber. Because of the integral location sensor, the spatial coordinates of every voxel in the imaged section are known.

Using known voxel locations, the processor can use the position measurements to compensate for probe movement and to average the 3D volume images that the 2D transducer array acquires, without losing (and with possibly improving) spatial resolution.

Furthermore, the position measurements eliminate the need to correlate between imaged volumes and match them. In more detail, with the disclosed technique, by knowing the position and orientation of the sensor attached to the 2D ultrasound transducer (3D image) a calibration can be made to calibrate the 3D image voxels to the coordinate system of the position sensor. Thus, by knowing the position and orientation of the sensor, the position of every voxel in the 3D ultrasound image is defined in the same coordinate system of the location sensor. When acquiring multiple 3D images at different orientations and positions, the information can be displayed according to the position of every voxel in the same coordinate system without a need to register or stick the ultrasound images using various correlation functions.

One possible use-case of such a catheter is to perform ultrasound imaging using the catheter and, at the same time perform an invasive electrophysiological (EP) procedure, such as ablation. During the EP procedure, the 4D ultrasound catheter may be used to image other entities used in the procedure, such as an ablation catheter. It is advantageous that the entity appears centered in the generated ultrasound images.

Some embodiments of the present invention use the fact that the scanned position of the wedge beam of ultrasound generated by the 2D array of transducers can be electronically steered. The direction, as well as the shape, of the wedge may be altered, within limits, by adjusting the phases of the driving signals of the respective individual transducers of the 2D array.

In an embodiment, a processor provides driving signals for the ultrasound transducers, to emit an ultrasound beam having a predefined field of view (FOV), and analyzes the received signals from the transducers to find the position of a target object (e.g., tip of an ablation catheter) within the wedge beam. The processor estimates a position of a target object within the FOV, and, when the estimated position of the target object violates a centering condition, automatically modifies the FOV of the ultrasound beam to re-meet the centering condition. To find the position, the processor may analyze echo signals or perform image processing on a derived ultrasound image.

It should be understood, however, that the disclosed technique is not limited to maintaining a point of interest (e.g., a target object) in the center of the FOV. Rather, the disclosed technique may be configured to maintain a point of interest at any selected location within the FOV.

As noted above, based on the found position of the target object within the wedge, the processor adjusts the phases of the driving signals to steer the wedge, so that the position of the target object (the catheter or any other object, such as the transeptal region of the heart) is centered in a display showing the object inside the predefined FOV.

In some embodiments, if the amount of wedge steering by adjusting phases is predicted to be, or deemed, insufficient, the ultrasound catheter can be guided robotically to move in a controlled manner to center the target object in the image. This may entail having a robotic arm controlling the various controls of a handle of the catheter, and thus controlling the catheter with six degrees of freedom. The location sensor in the catheter gives the actual motion of a distal end of the catheter inside the organ.

In some embodiments, to keep the image of the target object centered in a display, the processor initially alters the phases of the transducers, as described above. However, as noted above, for relatively large movements of the target object, the phase alteration may not provide sufficient image centering capability. In this case, the processor provides signals to the robot holding the handle, so as to maintain a centered image.

To have closed loop control of the robotic centering, in some embodiments the processor receives location-sensor signals and transducer signals. The 2D ultrasound array emits a 3D wedge which allows the processor to both visualize (e.g., using image processing, or analysis at a level of the acquired echo data) and track the direction of motion of the target object as it moves. The tracking, and, optionally, the use of sensor indication of an actual position of the distal end of the catheter, allows the processor to easily provide adjustments to the robotic arm, to keep the image centered.

While the above description covers automatically modifying the FOV to re-meet the centering condition using electronic steering and/or catheter position steering, these two techniques are examples of "automatically modifying the FOV." Other ways are also possible, such as changing an angle at which the array points (e.g., using MEMS actuator in the catheter or any other actuator of angle, such as a piezo actuator).

Ultrasound images are typically noisy, and in addition, objects within the images, such as object edges, are often fuzzy. The problems are intensified in cardiac images because of the movement of blood and of the heart chambers being imaged. In some embodiments of the present invention, the processor averages images having the same classifications (as defined below, also called hereinafter "matching identification"), and displays an averaged image. To this end, images acquired by the 4D catheter are recorded, and, using signals from the integrated location sensor of the catheter, the processor classifies images according to catheter position and orientation.

In embodiment, the processor identifies, based on the location signals, a group of the ultrasound images having a matching FOV being the classification used. The processor averages the ultrasound images in the group, to produce an enhanced image, and displays the enhanced image to a user.

In some embodiments, the processor may further classify the images according to the cardiac phase at which they were acquired, e.g., with respect to an ECG signal. With regard to using ECG gating, during any given heartbeat there are periods of time (e.g., diastole phase) when the catheter and/or the chamber wall are relatively stationary, so that, assuming the rate of image acquisition produces multiple images during these periods, the images acquired during these periods may be averaged as described above without causing significant motion artifacts in the image.

Other types of classification may also be used in other embodiments, for example, absence of movement of the catheter and/or absence of movement of an object in the image. Classification based on catheter level of motion during acquisition can mitigate motion artifacts in an average image.

In an embodiment, the processor stores the images and their classifications in a memory. When the catheter acquires a new image, the new image is classified by the processor in the same manner as the stored images, and averaged with stored images having the same classifications. The newly averaged image is then displayed.

Yet other embodiments of the present invention relate to imaging of a 3D cardiac volume using multiple 2D ultrasound images. 2D ultrasound images that are generated as fan-shaped slices (e.g., using a 1D ultrasound array) are typically noisy. By rotating the fan, so as to produce multiple slices, a 3D volume can also be imaged, but the resulting 3D image will also be noisy. Noise is especially bad in cardiac images, because of the movement of blood and of the heart chambers being imaged. In some embodiments, the images are acquired using a catheter with a transducer array, typically a linear array, that is introduced into the heart. By acquiring multiple 2D fan-shaped images of the volume, the processor images a 3D cardiac volume. The noise in each of the 2D images is reduced by applying a Laplace transform to each image and filtering the Laplace spectrum (e.g., applying low-pass filtration in the s-domain of the Laplace transform to remove or suppress noise). The multiple transformed noise-suppressed 2D images are then combined by the processor to form a 3D inverse image. An inverse Laplace transform is applied to the 3D image, and the transformed 3D image is displayed.

In an optional embodiment, using location sensor signals from location sensor of the catheter, the processor registers the multiple acquired ultrasound slices before performing Laplace transform and combining the transformed slices.

System Description

FIG. 1 is a schematic, pictorial illustration of a catheter-based ultrasound imaging system 20 using a catheter 21 with a distal end assembly 40 comprising a 2D ultrasound-array 50 and a location sensor 52, in accordance with an embodiment of the present invention. Integral location sensor 52 is pre-registered with the 2D array 50 of catheter 21.

Specifically, sensor 52 is configured to output signals indicative of a position, direction and orientation of the 2D ultrasound transducer array 52 inside the organ. A processor of the system is configured to register multiple ultrasound image sections using the signal output by the sensor acquired by the 2D ultrasound transducer array 50, one with the other.

As seen, distal end assembly 40 is fitted at the distal end of a shaft 22 of the catheter. Catheter 21 is inserted through a sheath 23 into a heart 26 of a patient 28 lying on a surgical table 29. The proximal end of catheter 21 is connected to a control console 24. In the embodiment described herein, catheter 21 is used for ultrasound-based diagnostic purposes, although the catheter may be further used to perform a therapy such as electrical sensing and/or ablation of tissue in heart 26, using, for example, a tip electrode 56.

Physician 30 navigates distal end assembly 40 of catheter 21 to a target location in heart 26 by manipulating shaft 22 using a manipulator 32 near the proximal end of the catheter.

In an embodiment, 2D ultrasound-array 50, shown in detail in an inset 25, is configured to image a left atrium of heart 26. The recorded images are stored by processor 30 in a memory 37.

As seen in an inset 45, ultrasound-array 50 comprises a 2D array 50 of multiple ultrasound transducers 53. Inset 45 shows ultrasound-array 50 navigated to an ostium wall 54 of a pulmonary vein of the left atrium. In this embodiment, 2D array 50 is an array of 32×64 US transducers. The 2D array 50 is able to image a section of the inner wall of the ostium.

Because of the integral location sensor, the spatial coordinates of every pixel in the imaged section are known.

Control console 24 comprises a processor 39, typically a general-purpose computer, with suitable front end and interface circuits 38 for driving ultrasound transducers 53 (e.g., in a phased array manner that includes steering an ultrasound beam), and for receiving echo signals from transducers 53 for processor 39 to use. Interface circuits 38 are further used for receiving signals from catheter 21, as well as for, optionally, applying treatment via catheter 21 in heart 26 and for controlling the other components of system 20. Console 24 also comprises a driver circuit 34, configured to drive magnetic field generators 36.

During the navigation of distal end 22 in heart 26, console 24 receives position and direction signals from location sensor 52 in response to magnetic fields from external field generators 36. Magnetic field generators 36 are placed at known positions external to patient 28, e.g., below table 29 upon which the patient is lying. These position and direction signals are indicative of the position and direction of 2D ultrasound-array 50 in a coordinate system of the position tracking system.

The method of position and direction sensing using external magnetic fields is implemented in various medical applications, for example, in the CARTO™ system, produced by Biosense Webster, and is described in detail in U.S. Pat. Nos. 6,618,612 and 6,332,089, in PCT Patent Publication WO 96/05768, and in U.S. Patent Application Publications 2002/0065455, 2003/0120150, and 2004/0068178, whose disclosures are all incorporated herein by reference.

In some embodiments, processor 39 may be configured to operate array 52 in an electronic "sweeping mode" to image a large portion of a cardiac camber. In an embodiment, the imaged cardiac chamber (e.g., a left atrium) is presented to physician 30 by processor 39 on a monitor 27, e.g., in as a volume rendering 55.

Processor 39 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. For example, system 20 may comprise additional components and perform non-cardiac catheterizations.

Ultrasound Image Centering

Figure 2:
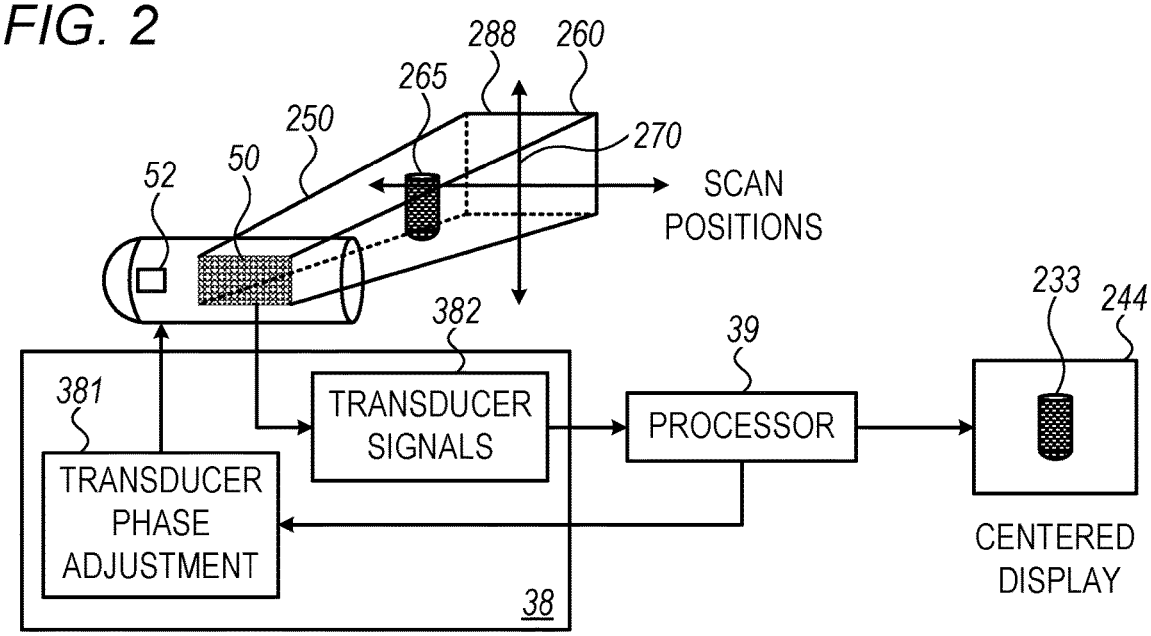
FIG. 2 is a schematic, pictorial illustration of a technique for ultrasound image centering by electronically steering the ultrasound beam of the ultrasound catheter of the system of FIG. 1, in accordance with an embodiment of the present invention.

FIG. 2 is a schematic, pictorial illustration of a technique for ultrasound image 244 centering by electronically steering the ultrasound beam of ultrasound catheter 21 of system 20 of FIG. 1, in accordance with an embodiment of the present invention. The electronic beam steering is done by processor 29 changing phases of driving signals of the phased array 52 of transducers 53 of catheter 21.

As seen, a 3D wedge 250 mode of acquisition enables simultaneous acquisition of a 2D image section 260 that captures a position 270 of an object 265 within a FOV 288 defined by wedge 250. Using location sensor 52, the geometry of ultrasound wedge 250 can be defined in a coordinate system of the location tracking system of system 20.

As noted above, ultrasound wedge 250 generated by the 2D array of transducers can be steered. Wedge 250 is an ultrasound beam having a predefined direction and FOV 288. The direction, as well as the shape of the wedge, may be altered, within limits, by adjusting the phases of the individual transducers of 2D array 50.

As seen, processor 39 provides driving signals via a transducer phase adjustment unit 381 of interface circuits 38 for the ultrasound transducers. Processor 39 analyzes the received signals (e.g., received echoes) from the transducers via a receiving unit 382 of interface circuits 38 and to find the position of target object 265 (e.g., of an ablation catheter) within the wedge (i.e., within FOV 288). Using unit 381, processor 39 adjusts the phases of the driving signals to steer the wedge, so that the position of the imaged catheter (or any other target object, such as the transeptal region of the heart) is centered in an image 244 showing the imaged (233) target object 265.

It should be understood that the disclosed technique is not limited to maintaining a point of interest (e.g., a target object 265) in the center of the FOV 288. Rather, the disclosed technique may be configured to maintain target object 265 at any selected location within FOV 288.

Figure 3:
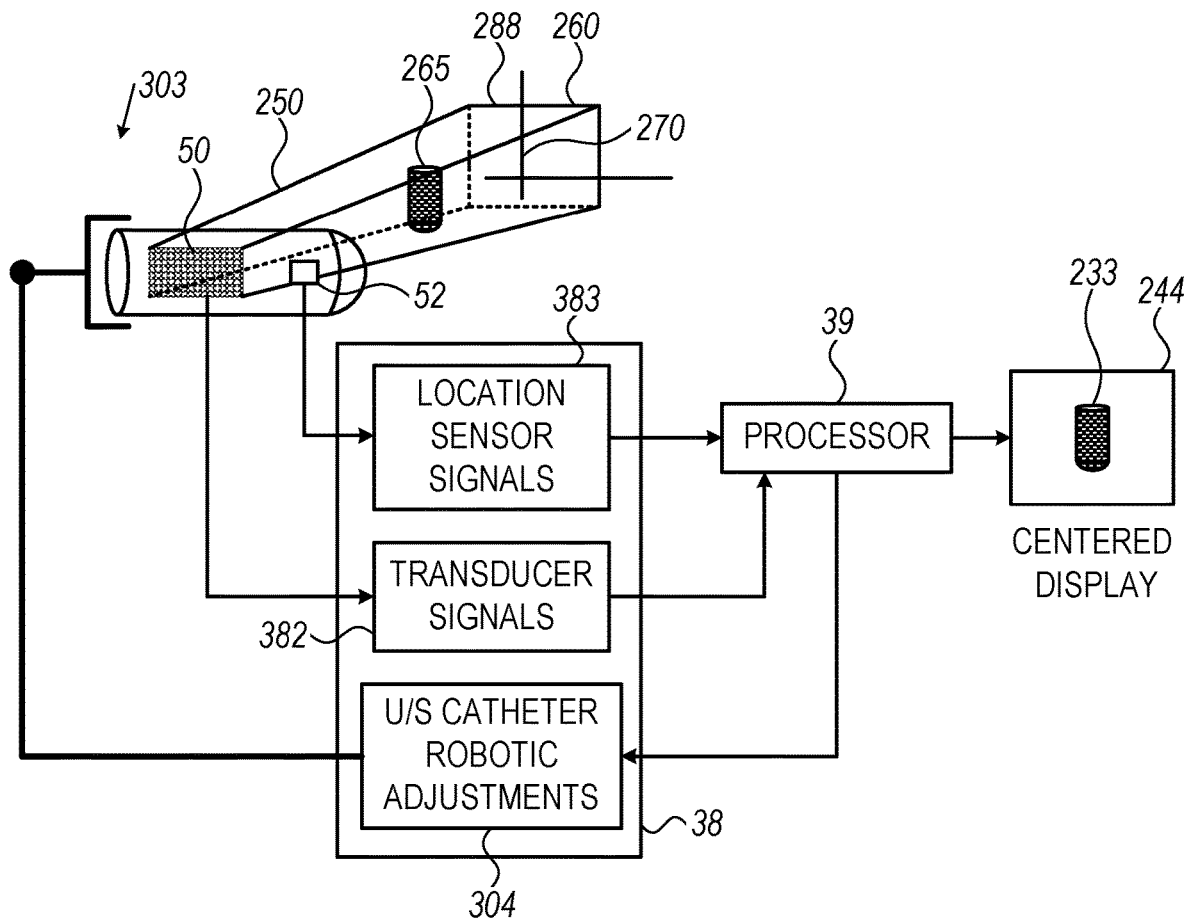
FIG. 3 is a schematic, pictorial illustration of a technique for ultrasound image centering using a robotic arm holding the ultrasound catheter of the system of FIG. 1, in accordance with an embodiment of the present invention.

FIG. 3 is a schematic, pictorial illustration of a technique for ultrasound image centering using a robotic arm 303 holding ultrasound catheter 21 of system 20 of FIG. 1, in accordance with an embodiment of the present invention.

Ultrasound catheter 21 is held robotically (303) when the amount of wedge steering by adjusting phases is deemed insufficient. The distal end of the catheter is moved by processor 39 commands in a controlled manner. Location sensor 52 in the catheter transmits signals indicative of the actual motion of the catheter.

As seen, processor 39 receives location sensor signals and transducer signals from location signals receiving unit 383 and from transducer signals receiving unit 382 of interface circuits 38, respectively. Typically, to keep the image of the target object centered in image 244, the processor initially alters the phases of the transducers, as described in FIG. 2 above. However, for relatively large movements of the target object (265), the phase alteration may not provide sufficient image centering capability. In this case, the processor provides signals, using robotic adjustment unit 304 of interface circuits 38, to robotic arm 303 holding the handle, so as to maintain the image centered within FOV 288.

The 2D ultrasound array gives 3D wedge 250 that allows the processor to visualize (e.g., using image processing, or analysis at a level of the acquired echo data) and track the direction of motion of the target object as it moves. The tracking allows the processor to easily provide adjustments to the robotic arm to keep image 233 centered in image 244, using the actual location of the catheter as conveyed by position signals via unit 383.

For example, using a geometric model of catheter 21, wedge 250 and the time of flight of the echo signals, processor 39 can instruct robotic arm 303 to move catheter 21 a given distance. Using location signals from sensor 52, the processor achieves a closed loop control of the motion so as to have a gross centering the object in real time, followed by fine tuning object 265 position 270 over FOV 288 by analyzing echo signals.

Figure 4:
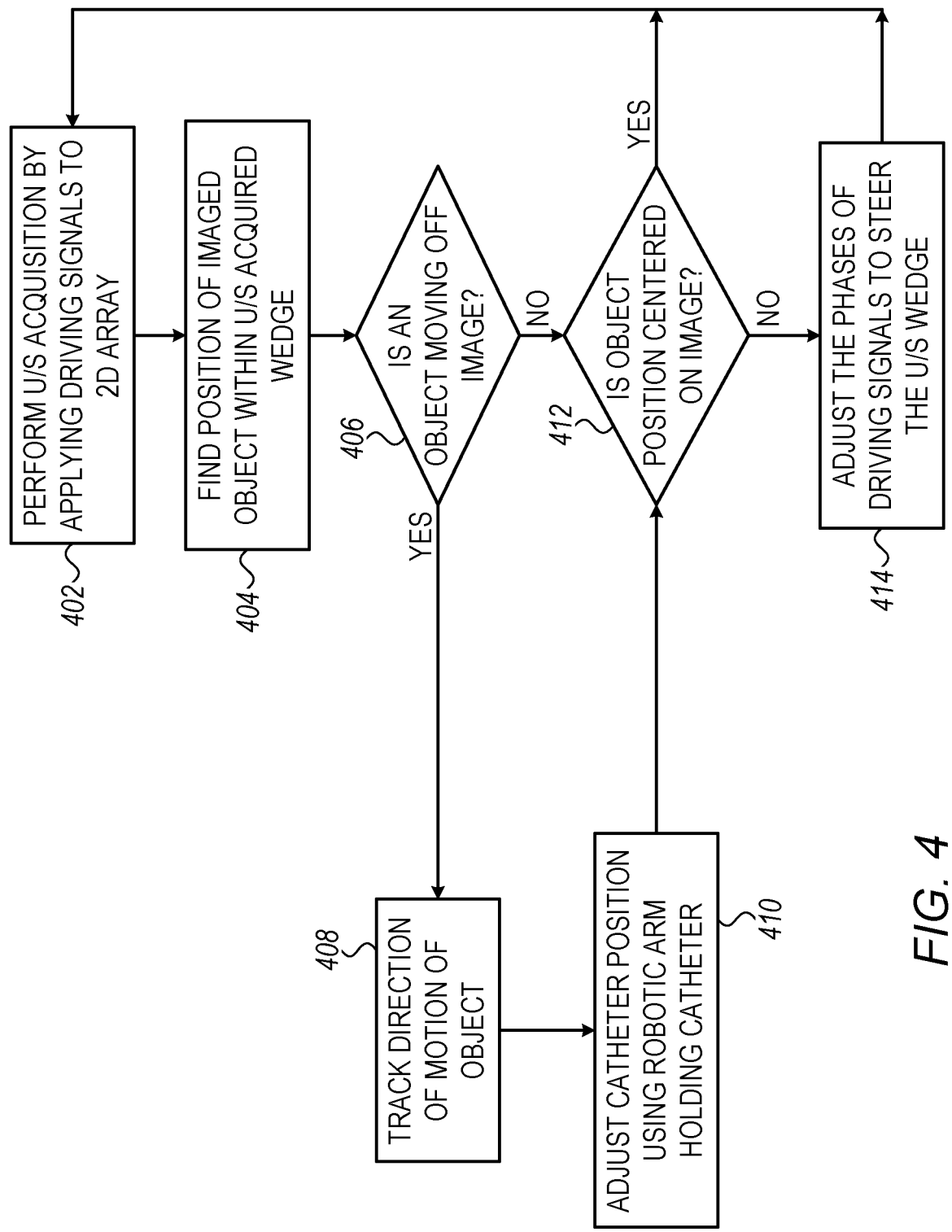
FIG. 4 is a flow chart that schematically illustrates a method for centering an ultrasound image using the robotic arm motion of FIG. 3 and the phased array beam steering of FIG. 2, in accordance with an embodiment of the present invention.

FIG. 4 is a flow chart that schematically illustrates a method for centering an ultrasound image using the robotic arm motion of FIG. 3 and the phased array beam steering of FIG. 2, in accordance with an embodiment of the present invention. The process begins by performing ultrasound (US) acquisition by processor 39 by applying driving signals to 2D-array 50, using unit 381, at US acquisition step 402.

Next, processor 39 analyses echo signals acquired by 2D-array 50 and transmitted using unit 382, to find position 270 of object 265 in ultrasound wedge 250, at a finding object position step 404.

If the processor identifies (406) a tendency of the object to move off FOV 288 (optionally also seen as off image 244), the processor analyzes a direction of motion, at a movement analysis step 408, and commands robotic arm 303 to move catheter 21 to center object 265 in FOV 288, at a robotic centering step 410.

If the processor identifies (406) that the object is not moving off FOV 288, within predefined tolerances, processor 39 checks if object 265 is shown (233) centered in image 244, at a displaying centering checking step 412.

If processor 39 finds the object is centered within predefined tolerances, the process returns to step 402 to acquire new data.

If processor 39 finds that the object is not centered within predefined tolerances, processor 39 adjusts the phases of driving signals of 2D-array 50 transducers 53, using unit 381, to steer wedge 250 so that the target object 265 is centered in image 244, at a displayed object centering step 414.

The flowchart of FIG. 4 is brought purely by way of example for the sake of conceptual clarity. In another example, the processor first steers wedge 250, and only if phased array steering is deemed insufficient does the processor command robotic arm 303 to move catheter 21. Thus, by way of example, the processor uses electronic steering for fine-tuning, and uses mechanical steering for coarse-tuning. The processor may use any other suitable logic.

Methods of Improving Ultrasound Image Quality

Figure 5:
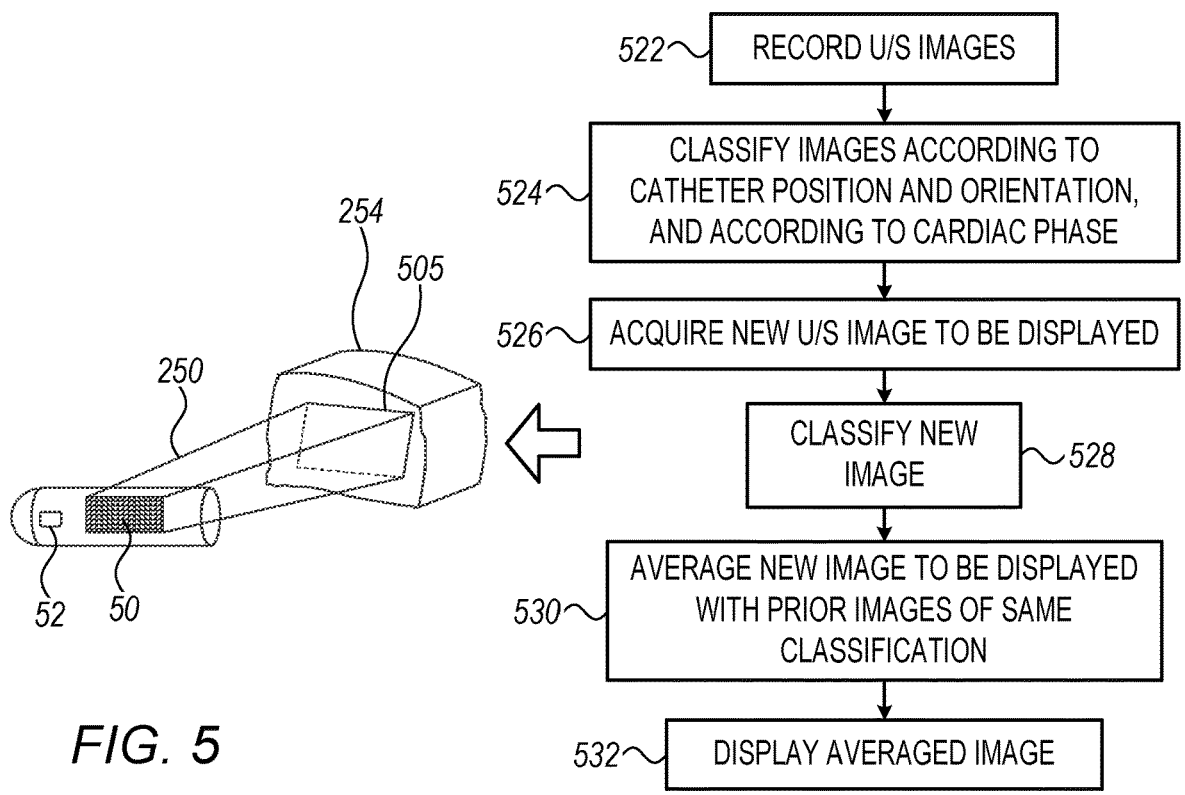
FIG. 5 is a flow chart that schematically illustrates a method for ultrasound image averaging, and an associated schematic, pictorial illustration of image acquisition using the catheter of FIG. 1, in accordance with an embodiment of the present invention.

FIG. 5 is a flow chart that schematically illustrates a method for ultrasound image averaging, and an associated schematic, pictorial illustration of image acquisition using catheter 21 of FIG. 1, in accordance with an embodiment of the present invention. The process begins with processor 39 recording US images acquired using catheter 21, at US images recording step 522. As seen, the images are of a section 505 of a cardiac wall tissue 254, at which wedge 250 is directed.

The process begins by performing an ultrasound acquisition inside a cardiac chamber, such as shown in FIG. 1, at a 4D ultrasound acquisition step 602.

Next, processor 39 classifies (i.e., identifies) recorded images according to catheter position and orientation, and according to cardiac phase determined using ECG, at US images classification step 524.

At a new US image acquisition step 526, processor 39 acquires a new US image using a US catheter.

The processor classifies the image at a new US image classification step 528. The processor then averages the image with other images of the same classification to produce an enhanced image, at an image averaging step 530.

Finally, processor 30 displays the average image on monitor 27, at a displaying step 532.

The images classified in step 524 and the new image classified 528 may be acquired using a same catheter or, rarely, acquired using different catheters.

Figure 6:
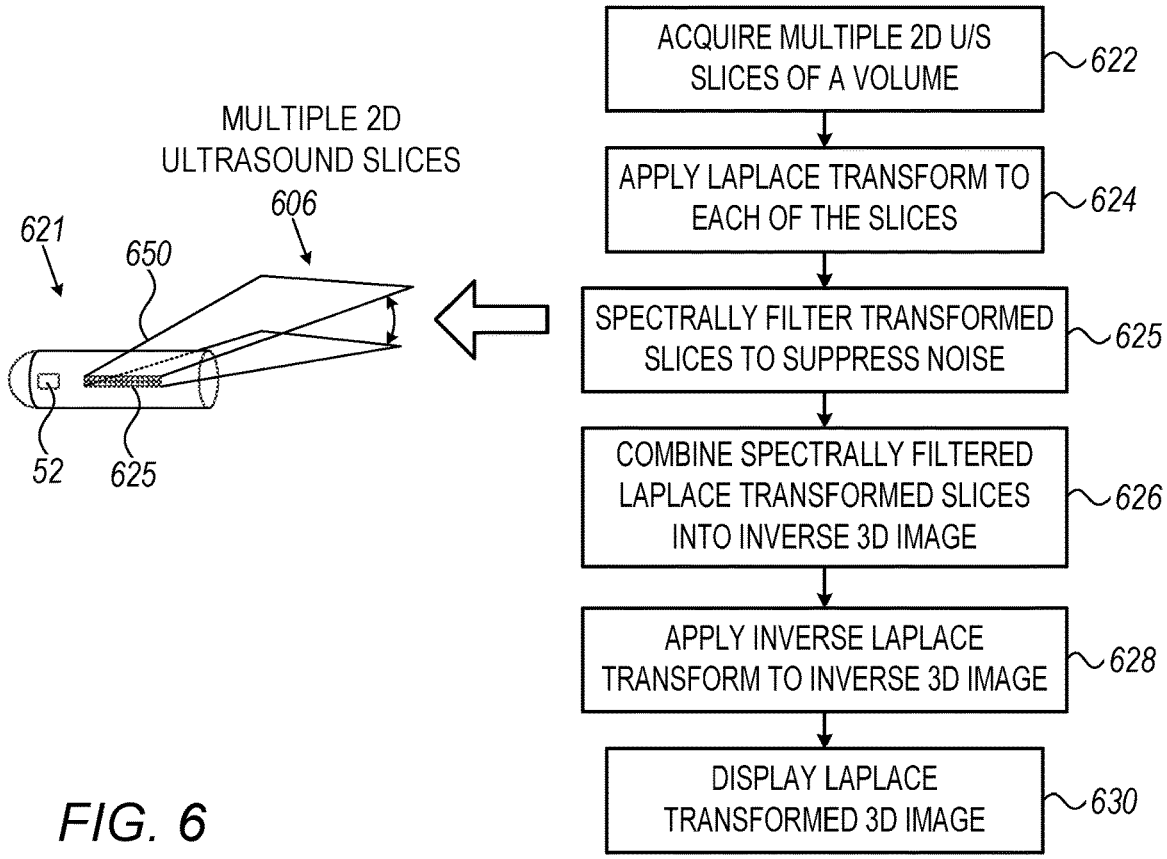
FIG. 6 is a flow chart that schematically illustrates a method for ultrasound image noise reduction, and an associated schematic, pictorial illustration of image acquisition using a 1D array ultrasound catheter, in accordance with an embodiment of the present invention.

FIG. 6 is a flow chart that schematically illustrates a method for ultrasound image noise reduction, and an associated schematic, pictorial illustration of image acquisition using a 1D-array 625 of ultrasound catheter 621, in accordance with an embodiment of the present invention.

The 1D ultrasound array 621 can be moved rotationally and, in this way, catheter 621 can generate a rotating fan 650 so as to acquire multiple slices 606, at a slices acquisition step 622.

At a Laplace transform step 624, processor 39 applies Laplace transform to each of the acquired 2D slices to reduce image noise of each of 2D slices 606.

Next, processor 39 spectrally filters the transformed slice, using for example digital low-pass filtering, to suppress noise in the transformed slices, at a noise suppression step 625.

The spectrally filtered slices are combined by the processor to generate a 3D Laplace transformed image, at a 3D Laplace transformed image generation step 626.

Next, the processor applies a higher dimension inverse Laplace transform, to generate a real 3D US image that is less noisy, at a 3D US image generation step 628.

Finally, the processor displays the 3D US image on a monitor, at a 3D US image displaying step 630.

Although the embodiments described herein mainly address cardiac applications, the methods and systems described herein can also be used in other body organs. For example, the disclosed technique can be used with transesophageal ultrasound device (TEE) devices visualizing the heart. As another example, the disclosed technique may be used for invasive ultrasound imaging of the lung, and for visualizing the liver and kidney.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   emitting an ultrasound beam, having a predefined field of view (FOV), from a 2D array of ultrasound transducers in a catheter in an organ of a patient;
   receiving in echo signals in response to the ultrasound beam;
   estimating a position of a target object within the FOV;
   when the estimated position of the target object violates a centering condition, automatically modifying the FOV of the ultrasound beam to re-meet the centering condition, wherein modifying the FOV comprises electronically steering the 2D array of ultrasound transducers by adjusting phases of one or more driving signals to the 2D array of ultrasound transducers;
   determining, based on the estimated position of the target object, that electronically steering the 2D array of ultrasound transducers is insufficient to meet the centering condition, and automatically controlling a handle of the catheter using a robotic arm configured to manipulate the handle to meet the centering condition.

2. The method according to claim 1, wherein modifying the FOV comprises automatically re-positioning the array relative to the organ.

3. The method to claim 2, wherein re-positioning the array comprises estimating a location of a distal end of the catheter using location signals from a location sensor integrated in the distal end, and moving the distal end based on the estimated location.

4. The method according to claim 1, wherein estimating the position of the target object comprises identifying the target object in an ultrasound image using image processing.

5. A system, comprising:
   a 2D array of ultrasound transducers in a catheter in an organ of a patient, the array configured to emit an ultrasound beam, having a predefined field of view (FOV), and to receive echo signals in response to the ultrasound beam; and
   a processor, which is configured to:
      estimate a position of a target object within the FOV;
      when the estimated position of the target object violates a centering condition, automatically modify the FOV of the ultrasound beam to re-meet the centering condition, wherein modifying the FOV comprises electronically steering the 2D array of ultrasound transducers by adjusting phases of one or more driving signals to the 2D array of ultrasound transducers;
      determining, based on the estimated position of the target object, that electronically steering the 2D array of ultrasound transducers is insufficient to meet the centering condition, and
      automatically control a handle of the catheter using a robotic arm configured to manipulate the handle to meet the centering condition.

6. The system according to claim 5, wherein the processor is configured to modify the FOV by automatically re-positioning the array relative to the organ.

7. The system to claim 6, wherein the processor is configured to re-position the array by estimating a location of a distal end of the catheter using location signals from a location sensor integrated in the distal end, and moving the distal end based on the estimated location.

8. The system according to claim 5, wherein the processor is configured to estimate the position of the target object by identifying the target object in an ultrasound image using image processing.

* * * * *